United States Patent [19]
Whitaker

[11] 3,955,706
[45] May 11, 1976

[54] AIR REFRESHENER AND DEODORIZED WASTE CONTAINER

[76] Inventor: William King Whitaker, 3601 N. Harrison St., Arlington, Va. 22207

[22] Filed: Mar. 19, 1975

[21] Appl. No.: 559,777

[52] U.S. Cl. .................................. 220/87; 220/1 T; 239/55
[51] Int. Cl.[2] ...................... B65D 25/00; A61L 9/04
[58] Field of Search ................. 220/87, 1 T; 239/53, 239/54, 55, 56, 57

[56] References Cited

UNITED STATES PATENTS

| | | | |
|---|---|---|---|
| 2,303,073 | 11/1942 | Brown | 239/53 |
| 2,425,612 | 8/1947 | Gamber | 220/87 |
| 2,798,636 | 7/1957 | Ketchledge | 220/87 X |
| 3,596,833 | 8/1971 | Gould | 239/54 |

*Primary Examiner*—William Price
*Assistant Examiner*—Steven M. Pollard

[57] ABSTRACT

A deodorized waste container is provided with a built in deodorizer or air refreshener. The air refreshener can be an integral part of the interior wall(s) of the waste container or affixed to the container wall(s) by an adhesive. A preferred type of air refreshener of the latter type comprises a carrier of an absorbent material, a vaporizable air refreshening material and an adhesive means affixed to said carrier for attaching said carrier to the interior wall(s) of the waste container.

10 Claims, 3 Drawing Figures

AIR REFRESHENER AND DEODORIZED WASTE CONTAINER

BACKGROUND OF THE INVENTION

Various types of containers for waste products are in use in a kitchen, bathroom, nursery, workroom, professional office, garage and the like. Many kinds of odors and germs build up in these containers depending upon the waste products contained therein. It is desirable, therefore, to provide a waste container which has a built in deodorizer or air refreshener, and optionally, a disinfectant to overcome the problems outlined above.

SUMMARY OF THE INVENTION

This invention relates to a container for waste products having a vaporizable air refreshening material on or within interior wall(s) of said container, wherein the vaporizable air refreshening material is affixed to the interior wall(s) of the container by an adhesive or is an integral part of the interior wall(s) of the container.

In addition, this invention provides an air refreshener comprising (a) a carrier formed at least partially of an absorbent material, (b) a vaporizable air refreshening material positioned in said carrier, and (c) means affixed to said carrier for attaching said carrier to a structure to be refreshened.

DETAILED DESCRIPTION

The waste containers of this invention can be of any size, shape or configuration. However, for practical purposes it is preferred that the containers be of such size to be portable. Also, there is no limitation on the material of construction for the container. Any of the well known materials, e.g., metal, plastic, wood, etc. may be utilized.

Figure 1:
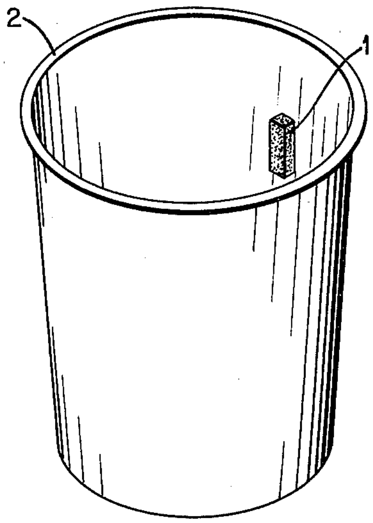
FIG. 1 is a view in perspective of a waste container having a vaporizable air refreshening material affixed to the wall of the container by an adhesive.

The vaporizable air refreshening material provides a built in deodorizer by being affixed to the interior walls of the container by an adhesive or by being an integral part of the interior wall of the container. FIG. 1 shows waste container 2 wherein vaporizable air refreshening material 1 is adhered by means of a pressure sensitive tape. This particular vaporizable air refreshening material is shown in greater detail in FIG. 3. Carrier 4, which is formed from an ester sponge having a generally rectangular shaped cross-section, has a solid vaporizable air refreshening cake 5 embedded therein. A sheet 7 of material, such as stiff paper or the like, is fixedly attached to the surface of the carrier 4 in overlying relationship to the air refreshening material 5. The outwardly directed surface of sheet 7 has a pressure sensitive layer of adhesive thereon which is covered by a protective sheet 6 (partially removed in FIG. 3).

Figure 3:
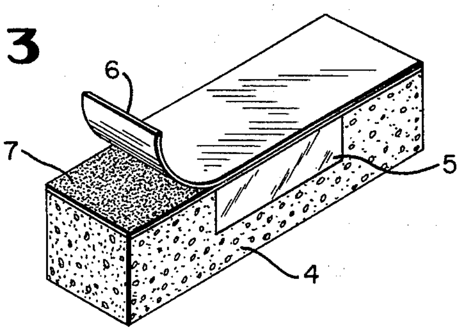
FIG. 3 is a sectional view of an air refreshener.

The air refreshener as exemplified in FIG. 3 is in and of itself a novel feature of this invention. It is a self-contained air refreshener which may be used and mounted in any desired location by removing the protective sheet 6 and simply pressing the adhesive layer onto a smooth, dry surface. Consequently, this air refreshener can be placed without any great effort at any desired location, e.g., waste cans, toilets, bathroom areas, etc.

Figure 2:
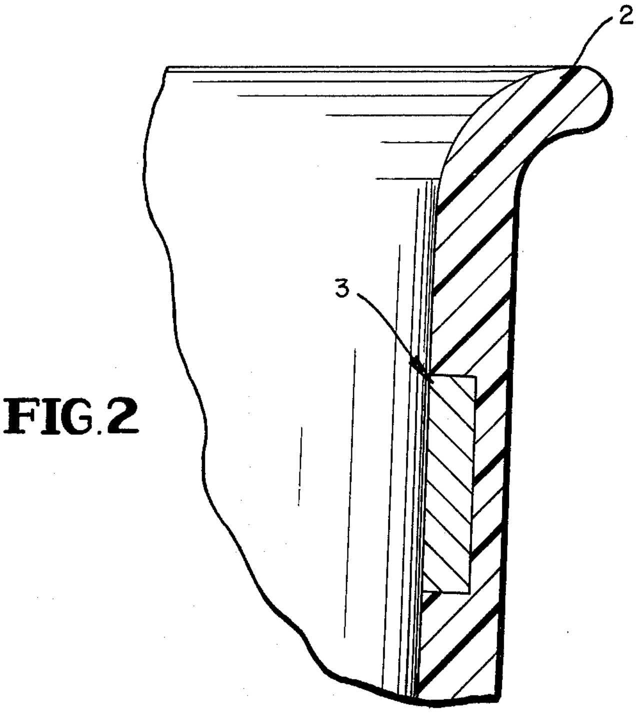
FIG. 2 is a perspective view of a waste container having a vaporizable air refreshening material as an integral part of the interior wall of said container.

FIG. 2 shows another embodiment of this invention wherein an air refreshening material 3 is actually incorporated into the interior walls of a waste container. For example, the refreshening material may be built into the side of the interior walls or be part of the interior walls of a plastic container.

The air refreshening material may be any of those well known and conventionally used for such purposes. A wide variety of perfumes, e.g., lavender, floral, fruity, etc. are suitable. Other deodorizers and/or disinfectants such as chlorophyll, formaldehyde, etc. may be used. Also, antimicrobioal agents such as hexachlorophene may be included in conventional amounts.

The invention and its broader aspects is not limited to the specific details shown and described, and departures may be made from such details within the scope of the disclosure without departing from the principles of the invention.

I claim:

1. A container for waste products having an air refreshener on interior wall(s) of said container, wherein the air refreshener comprises a sponge-like carrier having a solid vaporizable air refreshening material embedded therein.

2. A portable container in accordance with claim 1 wherein the air refreshener is adhered to the interior wall(s).

3. A portable container in accordance with claim 2 comprises a carrier formed at least partially of a sponge-like material and means affixed to said carrier for a attaching said carrier to a structure to be refreshened, wherein the means includes a strip of material affixed to the side of the carrier, said strip having a pressure sensitive adhesive on the outwardly directed surface thereof.

4. A portable container in accordance with claim 1 which is a synthetic plastic material.

5. A portable container in accordance with claim 4 wherein the air refreshener is located within a recess in a wall(s).

6. A portable container in accordance with claim 1 wherein the vaporizable air refreshening material also contains a disinfectant.

7. A portable container in accordance with claim 1 which is metal.

8. A portable container in accordance with claim 1 which is open-ended, having no cover attached thereto.

9. An air refreshener comprising (a) a carrier formed at least partially of a sponge-like material, (b) a solid vaporizable air refreshening material embedded in said carrier, and (c) means affixed to said carrier for attaching said carrier to a structure to be refreshened, wherein the means includes a strip of material affixed to the side of the carrier, said strip having a pressure sensitive adhesive on the outwardly directed surface thereof.

10. An air refreshener in accordance with claim 9 wherein the vaporizable air refreshening material includes a disinfectant.

* * * * *